(12) United States Patent
Schlachta et al.

(10) Patent No.: US 9,798,381 B2
(45) Date of Patent: Oct. 24, 2017

(54) HANDS-FREE POINTER SYSTEM

(75) Inventors: Christopher M. Schlachta, London (CA); Rajnikant V. Patel, London (CA); Ana Luisa Trejos, London (CA); Michael David Naish, London (CA)

(73) Assignee: London Health Sciences Centre Research Inc., London, Ontario (CA)

( * ) Notice: Subject to any disclaimer, the term of this patent is extended or adjusted under 35 U.S.C. 154(b) by 153 days.

(21) Appl. No.: 13/141,065

(22) PCT Filed: Nov. 20, 2009

(86) PCT No.: PCT/CA2009/001667

§ 371 (c)(1),
(2), (4) Date: Oct. 4, 2011

(87) PCT Pub. No.: WO2010/057304

PCT Pub. Date: May 27, 2010

(65) Prior Publication Data

US 2012/0032882 A1 Feb. 9, 2012

Related U.S. Application Data

(60) Provisional application No. 61/116,675, filed on Nov. 21, 2008.

(51) Int. Cl.
*G06F 3/01* (2006.01)
*A61B 1/00* (2006.01)

(52) U.S. Cl.
CPC .......... *G06F 3/012* (2013.01); *A61B 1/00039* (2013.01)

(58) Field of Classification Search
CPC combination set(s) only.
See application file for complete search history.

(56) References Cited

U.S. PATENT DOCUMENTS

| 6,753,847 B2 * | 6/2004 | Kurtenbach ....... G02B 27/2271 345/156 |
| 2002/0003528 A1 * | 1/2002 | Rosenberg .............. G06F 3/016 345/157 |
| 2003/0193572 A1 * | 10/2003 | Wilson ................... G08C 17/00 348/207.99 |

(Continued)

OTHER PUBLICATIONS

Atienza et al., Face Tracking Approch for the Development of Hands-Free User Interfaces, 2001, Image Processing and Communication, vol. 6, No. 3-4, 10 pages.

(Continued)

*Primary Examiner* — Chad Dicke
(74) *Attorney, Agent, or Firm* — Foley & Lardner LLP; Antoinette F. Konski; Lydia B. Choi

(57) ABSTRACT

The present invention describes a hands-free system for controlling the movement of a cursor on one or more display devices. A tracking device including a traceable marker and one or more accelerometers and gyroscopes are used to track position and acceleration of the marker relative to a target of interest. A processing means processes the motion signals from the tracking device to determine the location of the cursor on the operator's monitor, which may also be displayed on more monitors. The tracking device is worn by the operator, optimally on the operator's head. The operator's head movements determine movement of the cursor.

19 Claims, 6 Drawing Sheets

(56) References Cited

U.S. PATENT DOCUMENTS

| | | | |
|---|---|---|---|
| 2005/0027187 A1* | 2/2005 | Barth | A61B 6/5247 600/407 |
| 2005/0188316 A1* | 8/2005 | Ghanamgari | G06F 3/0386 715/743 |
| 2005/0202844 A1* | 9/2005 | Jabri et al. | 455/556.1 |
| 2008/0183190 A1* | 7/2008 | Adcox | A61B 17/8875 606/130 |
| 2008/0211768 A1* | 9/2008 | Breen | G06F 3/012 345/157 |
| 2008/0284729 A1* | 11/2008 | Kurtenbach et al. | 345/156 |
| 2009/0027337 A1* | 1/2009 | Hildreth | 345/158 |
| 2009/0058799 A1* | 3/2009 | Huang et al. | 345/156 |
| 2009/0139778 A1* | 6/2009 | Butler et al. | 178/18.03 |
| 2009/0292178 A1* | 11/2009 | Ellis et al. | 600/301 |
| 2010/0013767 A1* | 1/2010 | Gu et al. | 345/158 |
| 2010/0090877 A1* | 4/2010 | Dunbar et al. | 341/176 |
| 2010/0100359 A1* | 4/2010 | Podoloff et al. | 702/191 |

OTHER PUBLICATIONS

Flezer et al., Accessibility Research at the Department of Mechatronics at Darmstadt University of Technology, Jun. 2007, SIGACCESS newsletter, Issue 88, pp. 19-28.

Gorodnichy et al., Nouse 'use your nose as a mouse' Perceptual Vision Technology for Hands-Free Games and Interfaces, 2004, Image and Vision Computing, vol. 22, p. 931-942.

Hargrave-Wright, Improvements in Hands-Free Access to Computers, Oct. 2002, Technology and Standards Watch, report TSW 02-06, pp. 1-15.

Jayaraman et al., Novel Hands-Free Pointer Improves Instruction Efficiency in Laparoscopic Surgery, accepted at the SAGES Conference Apr. 10-12, 2008, 1 page.

Zhang et al., Human-Computer Interaction System Based on Nose Tracking, L. Jack (Ed), 2007, Human Computer Interaction, Part III, HCII, LNCS 4552, pp. 769-778.

* cited by examiner

HANDS-FREE POINTER SYSTEM

CROSS REFERENCE TO RELATED APPLICATIONS

This application is a national stage application under 35 U.S.C. §371 of International Application No. PCT/CA2009/001667, filed Nov. 20, 2009, which in turn claims the benefit under 35 U.S.C. §119(e) of U.S. Provisional Application Ser. No. 61/116,675, filed Nov. 21, 2008, the contents of each of which is hereby incorporated by reference into the present disclosure.

FIELD OF THE INVENTION

The present invention relates to novel systems, methods and devices useful for controlling the movement of a cursor on one or more display devices. Specifically, the present invention relates to novel hands-free systems, methods and devices useful for controlling the movement of a pointer on one or more display devices. The present invention more specifically relates to hands-free pointer systems, methods and devices to be used in situations wherein an operator controls a pointer on his or her monitor and the pointer is displayed on one or more monitors.

BACKGROUND OF THE INVENTION

Several different types of pointing devices allow for pointing to selected targets on a displayed image based upon manual user input. Examples of such pointer devices include conventional keyboards and pointing devices such as a mouse or a conventional laser pointer. Most input devices require a certain degree of manual dexterity. Physically challenged users (e.g., users without hands, or with permanent or temporary loss of motor skills) may have difficulty operating keyboards and conventional pointing devices.

A user may also be challenged by virtue of simultaneously performing another task such as, for example, a doctor operating on a patient and someone driving a car or operating machinery.

During many surgical procedures, a surgeon (instructor) is accompanied by an assistant (trainee) and/or surgical residents that are also undergoing training. The procedure itself requires the instructor and the trainee to work in close collaboration and to be in constant communication. During advanced minimally invasive surgical procedures (laparoscopic or robotics-assisted), the procedure is performed through small incisions while the surgical site is observed on several video monitors. Typically, during these procedures, the instructor and assistant trainee may each have both hands occupied by surgical instruments. In addition, both may have their own operating monitor on which the surgical image appears. Until now, during instruction the instructor would have to release one of his or her instruments and point to the trainee's monitor with a finger or other mechanical pointer to provide instruction. Some have adapted a laser pointer for this purpose, allowing the instructor to keep his or her hands occupied, but this still requires that the instructor turn away from his or her monitor and point onto the trainee's monitor. This is a time consuming, disorientating, and potentially uncomfortable practice.

Known types of pointing devices that allow hands-free control of a displayed image include speech-to-text converters. Various types of head tracking technologies also exist for controlling displayed images dependent upon movement of a user's head.

Zhang et al. ("Human-computer interaction system based on nose tracking," L. Jacko (Ed.), *Human Computer Interaction*, Part III, HCII 2007, LNCS 4552, pp. 769-778, 2007) and Gorodnichy et al. (*Image and Vision Computing*, vol. 22, pp. 931-942, 2004) introduce tracking systems that allow the user to control a pointer with movement of their nose. This type of technology uses a calibrated camera and image processing to identify the position of the nose in real-time. These are hands-free systems based on feature recognition and can be combined with vocal recognition.

Similarly, Atienza et al. (*Image Processing and Communications*, vol. 6, no. 3-4, pp. 47-60, 2001) describe a hands-free interface that is based on tracking facial features.

Felzer et al. (*SIGACCESS newsletter*, 88, pp 19-28, June 2007) present a hands-free control to assist disabled people. The hands-free pointer control system allows a pointer on a computer monitor to be controlled with a muscle-based interface consisting of a strap that is worn over the forehead.

Commercially available systems for hands-free pointer control include the SmartNav™ system. This system tracks the position of a reflective dot using infrared (IR) light. A problem with the use of IR light is that its use is susceptible to glare (J. Hargrave-Wright, "Improvements in hands-free access to computers," *Joint Information Systems Committee (JISC) Technology and Standards Watch*, Report # TSW 02-06, October 2002. Available: http://www.jisc.ac.uk/media/documents/techwatch/tsw_02-06.pdf).

Other hands-free pointer control systems include the Headmouse Extreme™ and the Tracker Pro™ by Madentec™. Another system, the Boost Tracer™, uses a gyroscope to detect head motion and control a pointer on a computer monitor.

Jayaraman et al. also describe a hands-free pointer that uses a camera to track the location of a marker placed on the surgeon's mask (Scientific Session of the Society of American Gastrointestinal and Endoscopic Surgeons (SAGES), Philadelphia, Pa., USA, Abstract #19547, P236, Apr. 9-12, 2008). This system demonstrated several difficulties including: accurate positioning of the pointer at the target site, degradation of the image quality and size, and cumbersome and complicated installation of required equipment.

The pointer systems of the prior art are insufficient in that: hand-held laser pointers systems are cumbersome and can only be used to point to one monitor at a time; there is no commercially available system for surgical training; pointer systems developed for remote collaboration require the use of a hand or a finger to actuate; most hands-free systems have been designed for disabled people, requiring movement of certain muscles or image processing to identify certain features on the user's face, which is not feasible for surgical applications since the surgeon is wearing a face mask, eye protection and a head lamp such that facial features are not exposed for tracking; systems based on gyroscopes or accelerometers have poor resolution and control at low speeds, although accuracy is critical in surgical training; systems based on infrared light are susceptible to glare or reflections occurring on other objects in the field of view of the light source leading to potentially critical errors; no system currently available combines marker tracking technology with inertial sensors; and none of the systems address the issue of velocity-dependent motion control providing precise pointer control at low speeds and large pointer displacement at high speeds.

In addition, none of the above mentioned hands-free devices have been adapted for specific situations such as during video-assisted operative procedures such as laparoscopic surgery and robotics-assisted surgery wherein the surgeon's hands are occupied manipulating surgical tools and the surgeon and trainee(s) may be using different monitors for guidance.

Therefore, what is required is a system, device and method that provide hands-free control of a cursor on a display device, such as a pointer on a monitor, that overcome the problems of the prior art. What is also required is a hands-free pointer that provides both accurate tracking and the ability to quickly move the pointer across the field of a monitor. Additionally, the hands-free pointer must not be susceptible to interference from other devices in a surgical environment, such as other lights and glare.

SUMMARY OF THE INVENTION

Novel systems, devices and methods have now been developed that are useful in providing accurate movement of a cursor on one or more display devices.

The present invention, in one aspect thereof, provides a system for controlling the movement of a cursor relative to a target displayed on one or more display devices characterized in that the system comprises: (a) a tracking means for tracking movement of an operator relative to the target, the tracking means operable to generate motion detection data as determined by the movement of the operator; and (b) a processing means for linking the motion detection data and at least one signal taken from the target to generate linked data, wherein the linked data serves to control movement of the cursor relative to the target on the one or more display devices.

The present invention, in another aspect thereof, provides a tracking device for use by an operator in a system for controlling the movement of a cursor relative to a target displayed on one or more display devices characterized in that the tracking device comprises a tracking means adapted to track movement of the operator relative to a target, the tracking means operable to generate motion detection data as determined by the movement of the operator.

The present invention, in yet another aspect thereof, provides a method for controlling movement of a cursor relative to a target on one or more display devices characterized in that the method comprises the steps of: (a) providing a tracking means for tracking movement of an operator relative to the target, the tracking means operable to generate motion detection data as determined by the movement of the operator; (b) using processing means for linking the motion detection data and at least one signal taken from the target to generate linked data, wherein the linked data serves to control movement of the cursor relative to the target; and (c) displaying the movement of the cursor relative to the target on the one or more display devices.

One or more advantages of at least some of the aspects described herein include: (1) a system that provides hands-free control of an object such as a pointer on a display device, (2) a system that provides high tracking accuracy of the object at all speeds, (3) a system that is not susceptible to external interference, (4) a system that is compact and easy to install, (5) a system that does not cause any loss of image resolution due to the addition of the object, (6) a system that does not require a personal computer or laptop.

DETAILED DESCRIPTION

Overview

Figure 1:
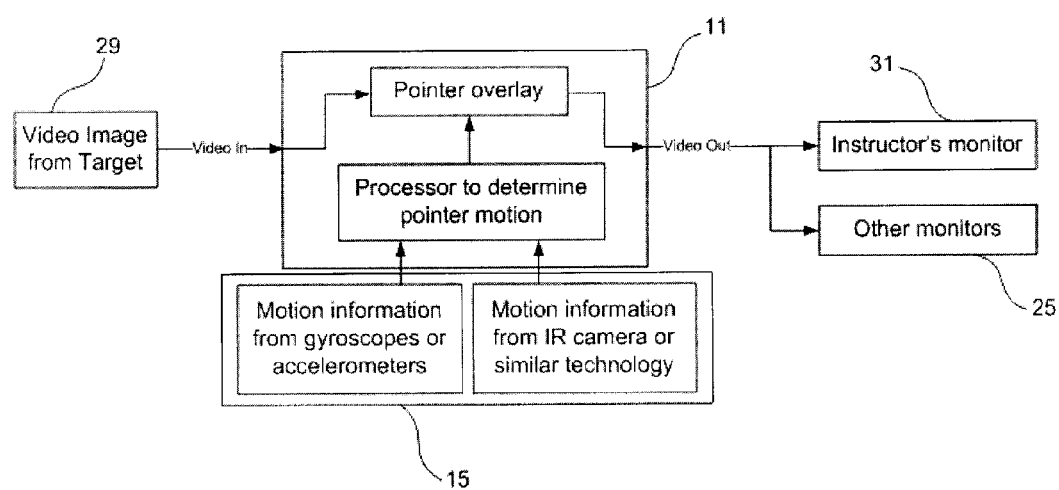
FIG. 1 illustrates a system for linking a traceable marker to pointers corresponding to more than one display device.

The present invention relates to systems, devices and methods for controlling the movement of a cursor relative to a target displayed on one or more display devices. The target may, for example, be an area of interest of an image displayed on the display device. In one aspect of the present invention it provides a hands-free controller of a cursor whose motion and position needs to be controlled.

A cursor includes any computerized reference point with respect to a display device, including for example a text cursor, pointer, crosshair, dot, arrow, plane indicator, triangle, or hollow circle. Furthermore, properties of cursor may be adjustable, including for example orientation, size, color and shape. The cursor may also be a plurality of cursors that can be individually activated for individual movement and adjustment.

In one aspect of the present invention it provides a system for controlling the movement of a cursor relative to a target displayed on one or more display devices. The system includes a tracking means that tracks movement of an operator relative to the target. The tracking means is operable to generate motion detection data based on the movement. A processing means is also provided for linking the motion detection data and a signal taken from the target to generate linked data. The linked data serves to control movement of the cursor relative to the target on the one or more display devices.

In another aspect of the present invention, one or more cursors may be provided. The system described herein may be a plurality of such systems, each operable to control a single cursor or a plurality of cursors as required. One or more tracking means and one or more processing means may be provided, wherein each tracking means and/or each processing means may be configured to control the movement of one or more of the cursors. The one or more tracking means may be provided for tracking movement of one or more operators.

In another aspect of the present invention it provides a system for a hands-free actuated video pointer or hands-free controller of any other video displayed cursor whose motion and position needs to be controlled, wherein the video pointer or cursor may be simultaneously displayed on one or more display devices, such as video monitors or projected displays, available in an activity room, and can be accurately controlled by an operator using a plurality of body movements.

The present invention may be useful for instruction and guidance of trainees (for example medical students, residents and fellows) wherein the instructor may be challenged by virtue of simultaneously performing another task. Examples of challenged instructors include a doctor operating on a patient, someone driving a car, an instructor operating machinery or an instructor having a physical challenge.

The present invention may also be useful for pointing to and selecting a target on a display device in a multitask situation wherein the user requires use of his/her hands to manipulate a device while pointing to a target. Non-limiting examples include playing computer games and gaming applications. The movement of a cursor can be controlled relative to the target. The user moves a marker relative to the target and a tracking means generates motion detection data from the marker. The motion detection data is linked to signal data from the target, such as an image of the target, to display the target and cursor.

The following discussion and examples concentrate on the application of the present invention in a surgical training scenario, however a person skilled in the art would comprehend these and other alternative implementations of the present invention as a natural extension of the present invention.

In order to best illustrate the present invention, it will be assumed that bodily gestures, and more particularly an operator's head gestures, are used to control movement of a cursor, since this may enable optimal use of the device when both the operator's hands are occupied as, for example, in a typical surgical scenario. Head gestures may include, for example, nodding, bobbing, and/or rotating left to right and vice versa.

Using the typical surgical scenario as an example, the cursor may appear on the video image of all display devices in the operating room, for example monitors displaying images from an endoscope, allowing an instructor/operator who may have both hands occupied performing surgery to provide instruction during the surgery by pointing to important anatomical features in a patient (the target), an image of which is also displayed on the display means.

It should be understood, however, that the present invention is implementable to a tracker for use in other modes of operation in addition to head gestures, including for example by blinking, foot pedals, shoulder movements, etc.

In another aspect the present invention may also be used to control cursors in a virtual environment using a hands-free means. Accordingly in one aspect the present invention may be used to provide training or instruction in a situation where the operator/instructor is located at a significant distance from the trainees but may provide training similar to that available while in the same room with the trainees. An example of this aspect of the invention comprises telementoring or telesurgery.

In yet another aspect of the present invention, the system for controlling the movement of a cursor relative to a target is provided as an interface to a typical computer system. Therefore, the system of the invention may be provided as a compact and easy to install device. A personal computer or laptop may therefore not be required to implement the system of the invention.

Furthermore, use of the present invention may allow a camera such as laparoscope or endoscope in a surgical setting, or a video camera attached to a computer, or any other camera capable of acquiring images of a target to maintain its resolution and provide real-time images of the target. The cursor may be linked to the target images by overlaying it upon the target images. In other words, there is no loss of resolution due to the addition of the hands-free pointer and the system of the present invention does not add any delay to the signal of the surgical camera.

Tracking Means

In accordance with the present invention, in one aspect thereof, the operator/instructor may use a device adapted to be worn by an operator, for example worn on the operator's head, including one or more markers (active and/or passive) and/or inertial sensors (accelerometer and/or gyroscope) that work in conjunction with the system described more fully below. The present invention may make use of a plurality of different sensing modalities to ensure accurate and optimal tracking of the instructor's head motion regardless of speed.

One benefit of the present invention over the prior art is that the operator's movements direct a video cursor rather than a physical object or pointer, meaning that the directed video cursor may appear simultaneously on all monitors linked to the camera that captures the video image of the target. By simply moving his or her head, the operator can move the video cursor and point to the image of interest to provide hands-free instruction. This is more ergonomic and efficient than currently available systems, since the operator is never required to take his or her eyes off of his or her own monitor to, for example, instruct trainees.

The tracking device may include one or more tracking means worn on any suitable part of the instructor's body, for example the instructor's head. One or more components of the tracking means may be in the form of a head band, a hat, or a clip-on device to attach to conventional head lamps or a mask, such as a surgical mask. The wearable tracking means may also be disposed on eyeglasses or on a headset or on an ear set. Optionally, the one or more tracking means is disposed on the wearable component in such a way that its weight is balanced to increase comfort and wearability. Optionally, parts of the tracking means may be disposed on the wearable portion and linked by wire or wirelessly to other parts of the tracking device not on the wearable portion, such as a belt clip or lanyard. This may help to reduce the weight of the wearable portion.

The tracking means may include one or more components.

One component of the tracking device may be one or more traceable markers, such as in the form of one or more reflective dots and/or one or more embedded active markers. An active marker may be used in conjunction with means to detect the position of the marker, such as one or more video-based tracking cameras. The active marker may be used in conjunction with a narrow wavelength modulated light source and detection means, which would be a beneficial source since it may eliminate potential interference from other lights or glare, which may be present, for example, in an operating room. One or more active markers may be provided for maximizing the possibility that at least one of the markers is visible to the detector. The motion information may also be provided using one or more typical infrared cameras or other similar technology. The use of a marker may ensure that regardless of the gear placed on the instructor's face (such as a face mask, goggles or other lights) the tracking system always has a fixed marker to follow.

Other components of the tracking device may be one or more accelerometers and/or one or more gyroscopes to provide information about the motion direction and speed of the tracking device, and correspondingly the operator's head. The use of accelerometers and gyroscopes generally, wherein a gyroscope provides angular velocity while an accelerometer provides linear acceleration, is known to those skilled in the art. In the context of the present invention, the accelerometers and/or gyroscopes may enable the system of the invention to sense the direction and speed of motion, which may enable the pointer system to display a cursor with a relatively higher accuracy and resolution compared to the pointer systems in the prior art. Furthermore, the accelerometers and gyroscopes are generally not affected by occlusions in the line-of-sight or optical noise (reflections or glare).

A further component of the tracking means may be, in the case of a wireless unit, a wireless transceiver and a power source to provide wireless communications with a processing means. Alternatively, the tracking means may be associated with the processing means using a wired transceiver system. Both wired and wireless transceiver systems and power sources for wireless transceiver systems are known to those skilled in the art.

The two main output signals of the tracking means may be provided by the accelerometer/gyroscope (A/G) combination and the video-based tracking camera. For cursor control purposes, an accelerometer may be used on its own, a gyroscope may be used on its own, or both may be used together. When attached to the instructor's head, for example, each sensor may be able to measure the acceleration of the head independently. Together, they may provide acceleration information in all degrees of freedom (or as many degrees of freedom as desired, based on the components used). The output from the A/G may be a voltage ($V_{out}$) that is proportional to these signals, such as: $\ddot{\theta}_{A/G}(x,y,z,\alpha,\phi,\gamma)=f(V_{out})$. As a result, acceleration may be measured regardless of the direction of motion, which may include rotation of the head, side to side motion, forward/backward motion, or up/down motion. Optionally, a hardware or software filter may be provided for filtering out tremors and other small head movements for increased accuracy.

A non-linear ballistics scheme may be used to map the movement of both the inertial sensor and vision sensor into a two-dimensional displacement in the cursor's local display coordinates. The shape of a corresponding ballistics curve, to configure the ballistics profile, may be configured and optionally saved through a user interface of the present invention. Nodes on the curve may be added, removed or configured for configuring a desired profile.

The tracking means may also include one or more cameras, which may track the position of the one or more markers, for example as attached to the instructor's head. Each camera may be at a fixed position so as to translate motion of the marker. Analysis of the video signals from the camera, or other sensor, may enable the position of the marker to be determined in two dimensions. Three-dimensional imaging may be provided by one or more three-dimensional display devices and virtual environments. Three-dimensional positioning could be enabled if a stereo or other "range finding" camera is used. The use of two or more markers may be provided for enabling three-dimensional tracking with a single or stereo cameras. Multiple-degree-of-freedom inertial sensors could also be provided for enabling three-dimensional tracking. The camera may be equipped with a filter, such as an infrared pass filter, that filters out light that does not correspond to the markers for rapidly detecting movement of infrared markers, and facilitating computationally efficient thresholding and blob detection algorithms.

Alternatively, the distance of the marker from the camera may be determined by measuring its apparent size. As the marker moves closer it may appear larger and as the marker moves away it may appear smaller.

Regardless of the methods used, the position of the marker may define motion detection data that may be a function of its three-dimensional coordinates relative to the camera: $\theta_T(x,y,z)$.

Processing Means

A processing means may be provided for interpreting the information provided by the various inputs provided by the tracking means.

Figure 3:
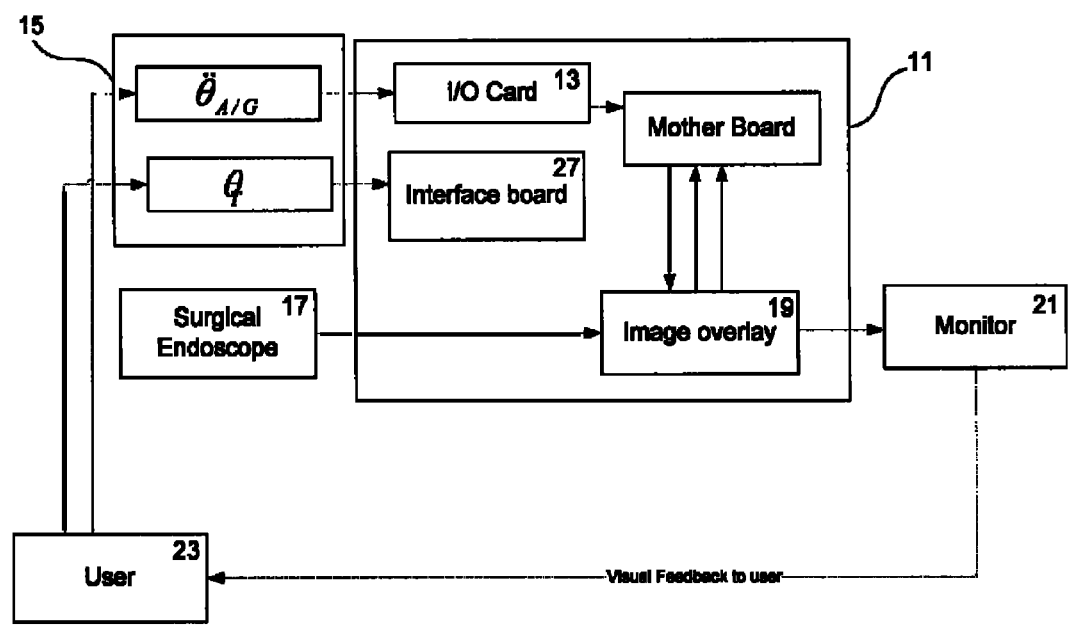
FIG. 3 illustrates a closed loop system for displaying a video image and overlaying a pointer thereupon.

FIG. 3 illustrates a closed loop, hands-free system for displaying an image and overlaying a cursor thereupon. The processing means 11 may include control hardware that itself may include an input/output (I/O) means 13 and/or an interface means 27. The I/O 13 or interface means 27 may include a central processing means enabling processing of the motion detection data received from the tracking means.

The central processing means may also include means for obtaining at least one signal taken from the target. For example, the signal may be an image signal and the central processing means may include what is generally referred to as a frame grabber that receives an image from, for example, an imaging means such as a video camera 17 (for example, a surgical endoscope).

The processing 11 means may also include an output means associated with one or more monitors 21. The output means may include an image overlay means 19 that is operable to link the motion detection data with the at least one signal taken from the target. The output means may also include an interface means for associating the processing means with the one or more monitors 21. Thus the target image may be displayed on the monitors 21 and the cursor location information overlaid thereupon. Correspondingly, as the user moves the marker, the motion detection data may be overlaid on the display device providing movement relative to the target image.

In one embodiment, the image overlay may be provided by incorporating a video overlay board (e.g., Matrox™ Vio™ Board) into the control system. The video board may stream the video from a camera in real-time without affecting the resolution of the image and without producing any noticeable time delay. The video board may also overlay the image of the cursor in real-time on top of the video image. Other ways of overlaying the two images could also be envisioned.

The processing means 11 may receive information from the tracking means, which may be used to determine movement and position of the cursor on a display device (monitor). The user 23 may look at the position of the cursor on the monitor 21 and adjust his/her head position according to the direction in which the cursor is to be moved, until it stops moving.

By fusing information from the different sensors the most accurate, robust and reliable estimate of the user's 23 head motion may be obtained and used to direct the motion of the cursor on the video monitors 21. The processing means 11 may use the motion detection data from the marker as one input, to orient the cursor relative to the monitor 21. As the operator moves his or her head across the camera, or other sensor, the cursor position may be calibrated. In addition, since one or more accelerometers and one or more gyroscopes may be included with the tracking device 15, the motion of the cursor may be adjusted to associate with the speed of the head motion using control schemes that are optimized for both high and low speeds. For example, low speed head motion may be associated with precise accurate cursor placement, whereas high speed head motion may be associated with rapid movement of the cursor over the area of the monitor. This fine/coarse control and positioning approach has not been described by the prior art, and may be of significant benefit in training or computer games scenarios.

FIG. 1 illustrates a system for linking a traceable marker to a cursor corresponding to more than one monitor wherein a video camera is used to generate the image of a target displayed on the monitors. The cursor may be provided on the monitors 25, 31 using means known by those skilled in the art. A tracking device 15, as described above, may be worn by the operator and a corresponding processing means 11, also described above, may be provided to trace the motion of the tracking device 15. By simply moving his or her head, the instructor can direct the cursor on the image 29 and provide hands-free instruction. This method of actuation is more ergonomic than current methods, since the instructor is never required to take his or her eyes off of his or her own monitor 31.

Figure 2:
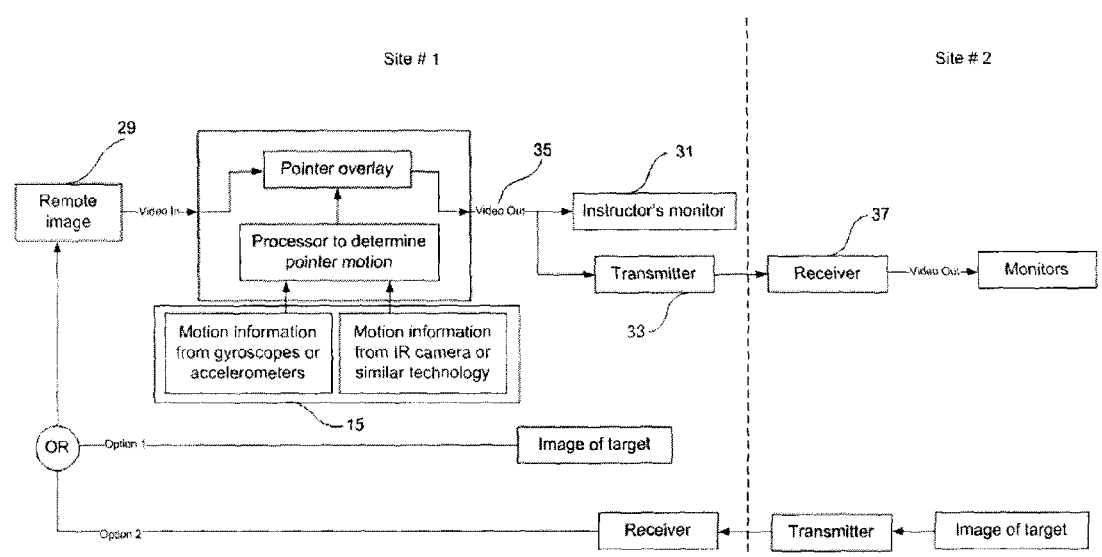
FIG. 2 illustrates a telementoring system that incorporates the overlay system previously illustrated in FIG. 1.

FIG. 2 illustrates a telementoring system that incorporates the cursor overlay system previously illustrated in FIG. 1. In addition to outputting video to the instructor's monitor 31, a transmitter 33 may be included for transmitting the video image 35 along with the cursor overlay to a remote receiver 37 at a location at which the trainees are attending.

The processing means may use either the A/G or video signals to control movement of the cursor on the display or in a three dimensional virtual environment. However, the present invention may also enable both motion signals to be used to complement each other when controlling the motion of a cursor on a display or in a virtual environment. Integration of the two signals may be accomplished by the options more fully described below, although the present invention is not limited to these integration options. The control system can constantly be monitoring both signals and comparing the achievable accuracy based on using each signal separately, or using both signals together. The present invention, however, is not restricted to A/G and the video signals. If other signals are used (apart from the A/G and video signals), the other signals could be combined in the same manner as fully described below.

There is a plurality of options for the integration of the A/G and video signals. Furthermore, some of these control loops can be combined together as necessary.

Figure 4:
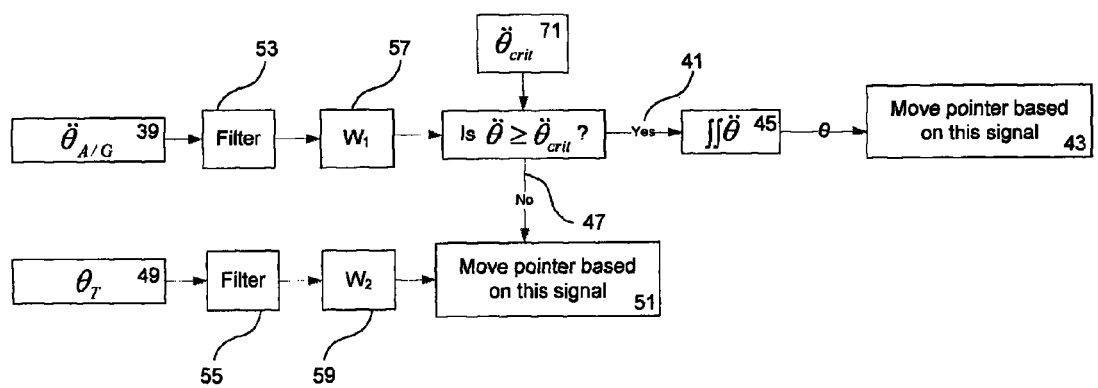
FIG. 4 illustrates what may be referred to as alternate integration of the accelerometer/gyroscope (A/G) signals and video signals.

FIG. 4 illustrates what may be referred to as alternate integration of the A/G and video signals. If the acceleration from the A/G signal 39 is higher 41 than a given critical or threshold value 71, the A/G signal may be used to move the cursor 43. The acceleration may be integrated twice 45 to obtain position information and the cursor may move relatively quickly when this is the signal that is used to control the position of the cursor. If the acceleration signal is lower 47 than the given critical or threshold value 71, then the information from the camera tracking the marker 49 may be used to adjust the cursor position 51. In this case, the cursor may move at a relatively low speed using a high resolution over the screen, such that the cursor can be accurately placed. Both input signals 39, 49 may be filtered 53, 55 and a weight function 57, 59 may be used to modify these signals as needed. The weight function 57, 59 and the critical or threshold value 71 for the acceleration may be determined empirically and may be set to fixed values, functions, fuzzy expressions, or a combination thereof. They may also be adjusted in real time (i.e., be adaptive) depending on the performance of the system.

Figure 5:
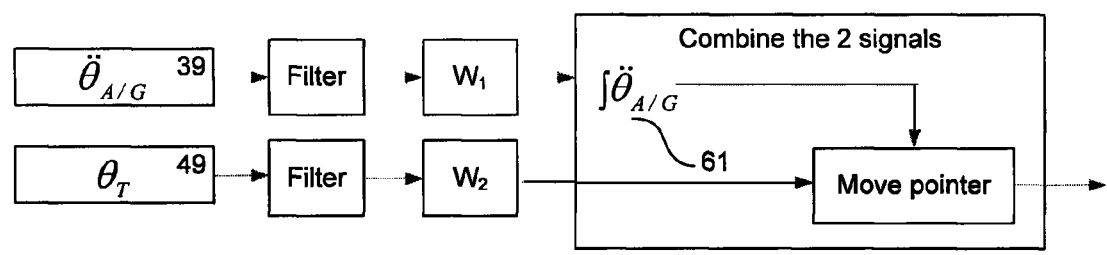
FIG. 5 illustrates what may be referred to as collaborative integration of the A/G and video signals.

FIG. 5 illustrates what may be referred to as collaborative integration of the A/G and video signals. The A/G 39 and video signals 49 may be combined at all times with this approach. The acceleration 39 may be integrated once 61 to determine the speed at which the cursor is moving, whereas the direction in which the cursor needs to be moved is determined by the position information 49 from the image-based tracking system. The speed information may also be related to the step size of the cursor movement: as the speed signal coming from the A/G decreases, the step size of the cursor as it moves across the screen may become smaller, and vice versa.

The tracking and processing means may also be used for self assessment, or recalibration, to evaluate how well the motion is being traceable by the signals.

Figure 6:
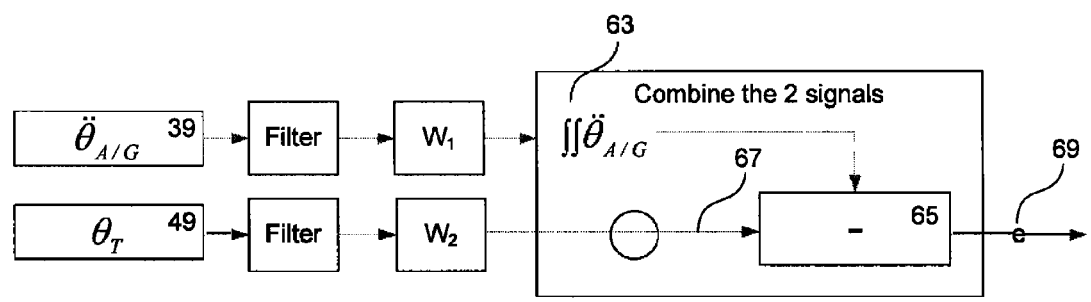
FIG. 6 illustrates evaluation of tracking error.

FIG. 6 illustrates the evaluation of tracking error. The acceleration from the A/G signal 39 may be integrated twice 63 to obtain a position signal. The resulting signal may be subtracted 65 from the position information 67 from the image based tracking system 49 to achieve an error measure 69. This evaluation may be used to assess the fidelity of the information being sensed. If the error 69 is too high, then it may be an indication that one or both signals are not being traced properly and recalibration might be required.

Any other functional approach to combining the A/G and video signals may also be used, as would be understood by a person skilled in the art.

In one aspect of the invention, the critical or threshold value may be initially determined empirically and then refined using optimization techniques (e.g., a minimax optimization that aims to minimize the maximum tracking error as illustrated in FIG. 6) or using a learning strategy (e.g., neural networks, reinforcement learning, fuzzy neural systems, etc.).

Using any of the above approaches, both signals may optionally be filtered to take out high frequency signals related to tremor and noise. Additionally, in the case of any possible malfunction, if one of the signals is absent, the other signal may be used exclusively as the sole provider of directional information and speed. For example, in the case of the marker being obstructed, the acceleration information can be integrated once to obtain speed and again to obtain position. The two signals can be used as described above to move the cursor, although typically this needs to be used only as a temporary measure as the accuracy may not be as high as in the ideal case.

A further implementation of the present invention may include a voice recognition means. For example, in addition to controlling system function by a single user, vocal recognition may be useful where more than one surgical expert is demonstrating a surgical technique. Any of the users may provide voice commands for operating one or more of the functions of the cursor. For example, the cursors for each of the respective surgical experts could be actuated and controlled by the surgeon who is speaking at the time. This may also be useful in video gaming applications wherein a cursor control is switched between players based on vocal prompts. Such applications may take place over remote links in which each user (surgeon/player) is equipped with a microphone, and optionally speaker or headset, for providing voice commands.

Voice recognition for controlling system function may include voice activation functions such as displaying/hiding the cursor; assigning a cursor color, shape, size, etc.; locking/unlocking cursor position; and/or activating/deactivating/changing any of the functionality described herein.

A locking function may also be provided. For example, the cursor may be locked to a particular feature of a displayed image. When the user or the camera moves, the cursor may remain locked to that feature. As the displayed image moves, the cursor may then move with the feature. If necessary, a processor such as a graphics processing unit (GPUs) may be provided for processing the images and maintaining real-time tracking.

Other variations and modifications of the invention are possible. As such modifications or variations are believed to be within the sphere and scope of the invention as defined by the claims appended hereto.

We claim:

1. A system for controlling the movement of a cursor relative to a target displayed on one or more display devices characterized in that the system comprises:
   a. wearable tracking device adapted to be worn by an operator for tracking movement of an operator, the wearable tracking device comprising (i) one or more accelerometers and one or more gyroscopes operable to generate motion detection data as determined by the movement of the operator and (ii) one or more wearable traceable markers moveable by the operator;
b. one or more cameras operable to generate track motion data of the one or more markers; and
c. a processor, the processor including (i) processor for determining cursor motion in communication with the wearable tracking device enabling processing of the motion detection data for determining movement and position of the cursor on the display device, the processor for determining cursor motion comprising instructions that, when executed, operate to (a) compare the one or more accelerometers and the one or gyroscopes motion detection data with the motion detection data from the one or more cameras, and (b) use the comparison of (a) to selectively use (I) only motion detection data from the one or more accelerometers and the one or more gyroscopes, (II) only track motion data from the one or more cameras or (III) a combination of motion detection data from the one or more accelerometers and the one or more gyroscopes, and track motion data from the camera, (ii) obtaining at least one signal taken from the target, (iii) an image overlay operable to overlay the processed motion detection data with the at least one signal taken from the target, and (iv) an output in communication with the one or more display devices to display the at least one signal taken from the target and the cursor location overlaid thereupon.

2. The system of claim 1 characterized in that the tracking device further comprises one or more wearable traceable markers moveable by the operator and one or more cameras operable to track motion of the one or more markers.

3. The system of claim 2 characterized in that each of the one or more markers is selected from the group consisting of a reflective dot and an active marker.

4. The system of claim 1 characterized in that the signal taken from the target comprises an image of the target obtained by a video camera.

5. The system of claim 1 characterized in that the system further comprises the one or more display devices.

6. The system of claim 1 characterized in that the system further comprises a wireless communication between the tracking device, the processor, and the one or more display devices.

7. The system of claim 1 characterized in that the cursor serves to select or point to the target on the one or more display devices.

8. The system of claim 1 characterized in that the system further comprises a transmitter in communication with the image overlay, and a receiver in communication with the transmitter, the transmitter operable to transmit the at least one signal taken from the target and the cursor location overlaid thereupon to the receiver to display the at least one signal taken from the target and the cursor location overlaid thereupon on one or more display devices linked to the receiver.

9. The system of claim 1 characterized in that the system further comprises vocal recognition, wherein the operator can control one or more functions of the system by one or more voice commands.

10. The system of claim 9 characterized in that the vocal recognition enables one or more additional operators to provide voice commands for enabling multiple-operator control of one or more cursors relative to one or more targets.

11. The system of claim 1 characterized in that the system is operable to track movement of the operator in three dimensions.

12. The system of claim 11 characterized in that the one or more display devices are three-dimensional display devices.

13. The system of claim 11 characterized in that the system further comprises a virtual environment and wherein the system is operable to control movement of the cursor relative to the target in the virtual environment.

14. The system of claim 1 characterized in that a mapping scheme is used to generate the motion of the cursor by mapping the movement of the operator to a two-dimensional displacement.

15. The system of claim 1 characterized in that the processor implements fine/coarse control based on the motion detection data of the one or more accelerometers and one or more gyroscopes.

16. The system of claim 1, wherein relatively low speed body part motion is associated with relatively accurate cursor placement, and relatively high speed body part motion is associated with relatively rapid movement of the cursor over the one or more display device.

17. The system of claim 1, wherein the wearable movement and speed tracking device is a hands-free movement and tracks speed.

18. A method for controlling movement of a cursor relative to a target on one or more display devices characterized in that the method comprises the steps of:
a. providing a wearable tracking device for tracking movement of an operator, the tracking device comprising: one or more accelerometers and one or more gyroscopes operable to generate motion detection data as determined by the movement of the operator, and one or more wearable traceable markers moveable by the operator;
b. providing one or more cameras operable to track motion of the one or more wearable traceable markers;
c. using a processor means for: (i) receiving and processing the motion detection data from the one or more accelerometers (A), from the one or more gyroscopes (G) and from the one or more cameras, (ii) receiving and processing the motion detection data from the one or more cameras, (iii) comparing the AG motion detection data with the motion detection data from the one or more cameras, (iv) using the comparison of (iii) for selecting AG motion detection data, motion detection data from the one or more cameras, or from a combination of AG and the one or more cameras, and (v) determining movement and position of the cursor on the one or more display devices based on the motion detection data selected in (iv); and
d. displaying the linked data on the one or more display devices, thereby controlling movement of the cursor relative to the target on the one or more display devices.

19. The method of claim 18 characterized in that each of the one or more wearable traceable markers is selected from the group of a reflective dot or an active marker.

* * * * *